United States Patent [19]

Takruri

[11] Patent Number: 5,272,135
[45] Date of Patent: Dec. 21, 1993

[54] METHOD FOR THE STABILIZATION OF METHIONINE-CONTAINING POLYPEPTIDES

[75] Inventor: Harun Takruri, Newport Beach, Calif.

[73] Assignee: Chiron Ophthalmics, Inc., Irvine, Calif.

[21] Appl. No.: 663,021

[22] Filed: Mar. 1, 1991

[51] Int. Cl.$^5$ .................. C07K 15/00; C07K 17/00
[52] U.S. Cl. ........................ 514/12; 514/21; 530/399
[58] Field of Search ............ 530/397, 399, 300, 350, 530/345; 514/12, 21, 2, 8, 973

[56] References Cited

U.S. PATENT DOCUMENTS 4,835,254  5/1989  DiMarchi et al. ............... 530/345

OTHER PUBLICATIONS

CA 100:144972z, Green Cross.
J. Parenteral Science and Technology, 42:1988, "Parenteral Formulations of Peptides, Proteins and Stabilizers", Chay et al., S3–S26.

*Primary Examiner*—Jeffrey E. Russel
*Assistant Examiner*—P. Lynn Touzeau
*Attorney, Agent, or Firm*—Rothwell, Figg, Ernst & Kurz

[57] ABSTRACT

A method for inhibiting the oxidation of a polypeptide in a liquid or semi-solid pharmaceutical or therapeutic preparation, the polypeptides having an amino acid sequence comprising at least one methionine residue, wherein the amino acid methionine is added in a sufficient amount to inhibit the oxidation of the methionine residue(s) to methionine sulfoxide.

25 Claims, 4 Drawing Sheets

METHOD FOR THE STABILIZATION OF METHIONINE-CONTAINING POLYPEPTIDES

BACKGROUND OF THE INVENTION

This invention relates to a method of inhibiting the oxidation of a polypeptide in a liquid or semi-solid medium, the polypeptide having an amino acid sequence comprising at least one methionine residue. More specifically, the invention relates to a method of inhibiting the oxidation of a tissue growth factor in a liquid or semi-solid medium, wherein the amino acid sequence of the tissue growth factor comprises at least one methionine residue. The invention further relates to stabilized, pharmaceutically effective preparations of such polypeptides.

In recent years, researchers have developed numerous techniques that have made possible the production and purification of various polypeptides on a commercial scale for therapeutic and pharmaceutical purposes. For example, polypeptides such as epidermal growth factor can be employed as the pharmacologically active component in ophthalmic preparations employed to enhance the repair of ocular tissue and also in cornea storage media employed in preserving eye tissue prior to surgical transplantation, i.e., keratoplasty. In particular, epidermal growth factor has been shown to have wound healing promoting activity (*Plast. Reconstr. Surg.*, 64,766 (1979); *J. Surg. Res.*, 33,164 (1982)); anti-inflammatory activity and analgesic activity (Japanese Laid-open Patent Publication No. 115785/1985). Epidermal growth factor is just one of a number of growth factors which are low molecular weight polypeptides that have the ability to stimulate the repair and maturation of tissue when applied thereto.

A growth factor can be selective with regard to both the type of tissue it acts upon as well as the extent of stimulation it causes in responsive cell types. For example, epidermal growth factor (EGF), vaccinia growth factor (VGF), nerve growth factor (NGF), platelet-derived growth factor (PDGF), fibroblast growth factor (FGF), transforming growth factor alpha (TGF-$\alpha$), transforming growth factor beta (TGF-$\beta$), and insulin-like growth factor I (IGF-I) are all low molecular weight polypeptides which possess the ability to stimulate the division and maturation of certain cells.

The growth factors are known proteins, the properties and biological activities of which have been are described, for example, in review articles by Krisis et al., *Biotechnology*, February, 1985, pp. 135-140 and in *Hormonal Proteins and Peptides*, Ed. by Chao Hao Li, Vol 12, "Growth Factors" Academic Press (1984).

Epidermal growth factor is a low molecular weight protein (6040 daltons has been reported) previously isolated from mouse salivary glands according to the method of Savage and Cohen, *J. Biol. Chem.*, 1972; 257; 7609-11. European Patent Office publication number EP 177,915 teaches the production of recombinant human EGF (rhEGF) by *E. coli* transformed with a vector containing DNA encoding EGF.

A process for obtaining transforming growth factor alpha is described in J.E. DeLarco and G.E. Todaro, "Growth Factors From Marine Carcoma Virus-Transformed Cells", *Proc. Natl. Acad. Sci. U.S.A.*, 75:4001-4005, 1978.

EP 219,814 teaches the production of recombinant human insulin-like growth factor. I.E. Rinderknecht and R.E. Humbel teach the production of insulin-like growth factor I in "Polypeptides with the Non-Suppressible Insulin-Like and Cell-Growth Promoting Activities in Human Serum: Isolation, Chemical Characterization and Some Biological Properties of Forms I and II", *Proc. Natl. Acad. Sci. U.S.A.*, 73:2365-2369, 1976.

Vaccinia growth factor is obtained from vaccinia virus-infected cells according to the methods of D.R. Twardzik, J.P. Braun, J.E. Ranchalis, G.E. Todaro and B. Moss, "Vaccinia Virus-Infected Cells Release A Novel Polypeptide Functionally Related To Transforming and Epidermal Growth Factors", *Proc. Natl. Acad. Sci. U.S.A.*, 82:5300-5304, 1985.

Pharmaceutical preparations containing growth factors in an aqueous medium, such as ophthalmic preparations of EGF, commonly are packaged in plastic containers made of low density polyethylene (LDPE) or polypropylene for convenient storage and application. However, these plastic containers are readily permeable to oxygen. The oxygen causes rapid oxidation of the methionine residue(s) in the growth factor to methionine sulfoxide. It is the side chain of the methionine residue which is particularly vulnerable to oxidation (Manning et al., *Pharmaceutical Research*, Vol. 6, No. 11, 1989). Although the growth factor is still biologically active after its methionine residues have been oxidized to methionine sulfoxide, the growth factor is not acceptable for pharmaceutical use according to the standards of regulatory agencies, such as the FDA, when high levels of methionine sulfoxide are present. Current precautionary procedures to try to exclude oxygen during the manufacture and packaging of the preparation have proven to be ineffective in preventing significant methionine oxidation. The result is that the pharmaceutical preparation has a shorter effective life than is potentially possible if the oxidation reaction could be inhibited. In addition to growth factors, oxidation has been observed in many methionine containing peptide hormones during their isolation, synthesis and storage. Examples of some of the polypeptide hormones include adrenocorticotropic hormone, human growth hormone or somatotropin and the like.

Certain amino acids and various combinations thereof and surfactants, such as polysorbate and poloxamer and the like have been used to stabilize peptide and protein compositions. See, for example, Yu-Chang, John Wang and Musetta A. Hansen, "Parenteral Formulations of Proteins and Peptides: Stability and Stabilizers", *Journal of Parenteral Science and Technology*, 42:S14, 1988. However, none of the amino acids or surfactants are used to deter the oxidation of methionine residues to methionine sulfoxide in a liquid or semi-solid medium.

Therefore, there is a need for a method of inhibiting the oxidation in pharmaceutical vehicles of polypeptides having an amino acid sequence which comprises at least one methionine residue.

SUMMARY OF THE INVENTION

In accordance with the present invention, a method for inhibiting the oxidation of a polypeptide characterized by an amino acid sequence comprising at least one methionine residue comprises adding methionine to the medium in an amount effective to inhibit the oxidation of the methionine residue. The added methionine stabilizes the preparation containing the polypeptide by inhibiting the rapid oxidation of the methionine residue(s) to methionine sulfoxide. Polypeptides that can be stabilized in this manner include the tissue growth factors. In the preferred embodiment, the polypeptide is an epidermal growth factor.

DETAILED DESCRIPTION OF THE INVENTION

Figure 1:
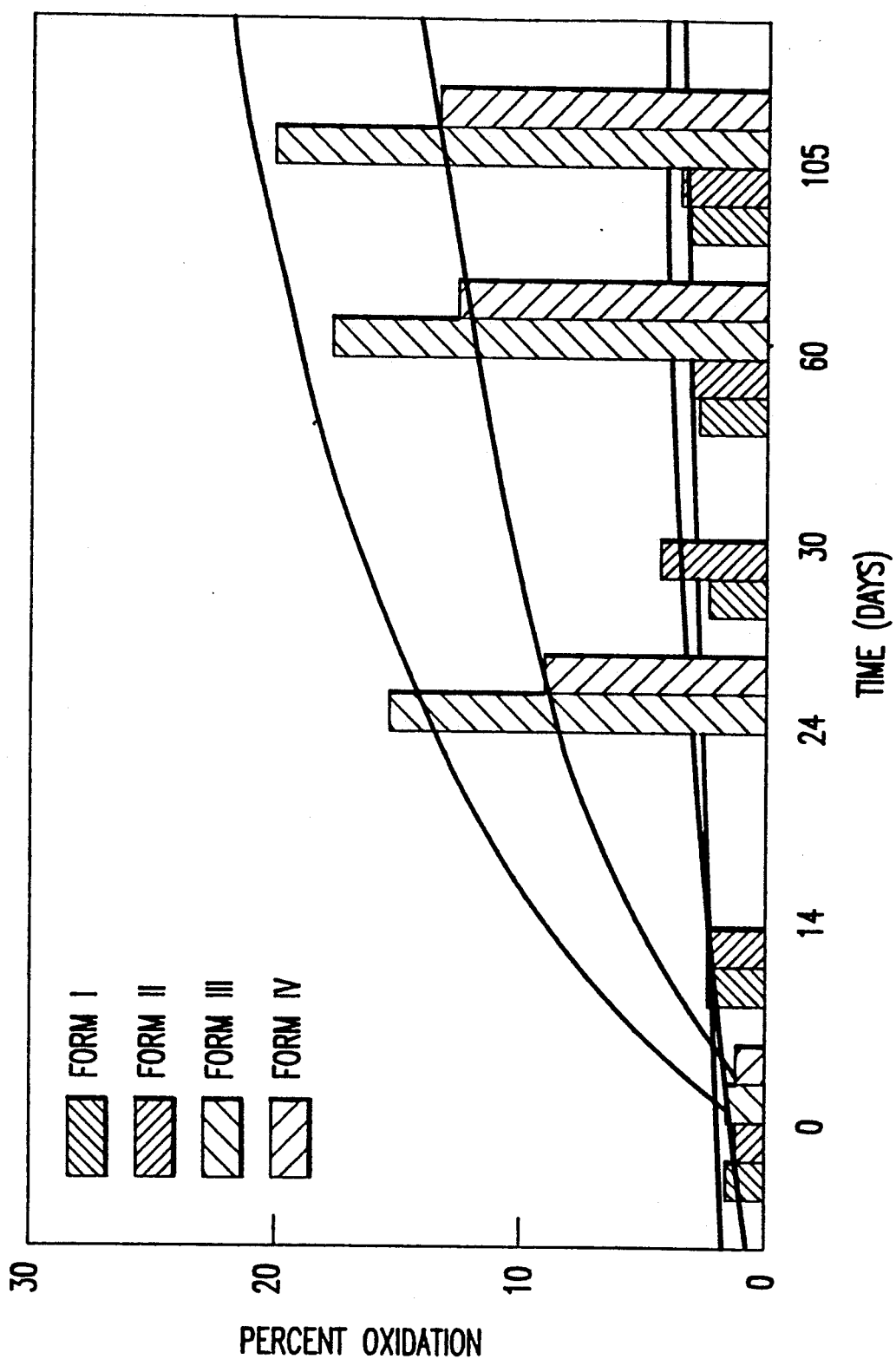
FIG. 1 illustrates the oxidation rates of four different formulations of recombinant human epidermal growth factor (rhEGF) acetate at 4° C. over a 105 day time period.

In accordance with the present invention, the addition of the amino acid methionine to liquid or semi-solid compositions comprising methionine-containing polypeptides stabilizes the compositions. Such compositions include, for example, therapeutic and pharmaceutical preparations and tissue storage media. The added methionine stabilizes the preparation by inhibiting the oxidation of the polypeptide's methionine residue(s) to methionine sulfoxide.

As used herein, the term "polypeptide" encompasses natural, synthetic and recombinant polypeptides having a desired biological activity, including polypeptides having deleted, replaced or altered amino acid sequences in comparison with the full-length natural polypeptide or biologically active fragments thereof.

In practicing the preferred embodiment of this invention, methionine is added to a pharmaceutical preparation, such as an aqueous ophthalmic preparation, comprising a methionine-containing growth factor, such as epidermal growth factor, in sufficient quantity to inhibit the oxidation of the methionine residue to methionine sulfoxide. Any stereoisomer of methionine (L, D or DL isomer) or combinations thereof can be used. The resulting ophthalmic composition remains stable for a longer period of time than if methionine had not been added.

The method and composition of the present invention will be further described with particular focus on ophthalmic aqueous-based compositions of a growth factor such as EGF. It is to be understood, however, that the present invention can be used by those with ordinary skill in the art to stabilize other aqueous or semi-solid polypeptide compositions.

Ophthalmic compositions comprising EGF can be used for the restorative process of the corneal epithelium in nondystrophic diseases of the eye, for example herpetic lesions. See, for example, Salvatore Daniele et al., "The Effect of the Epidermal Growth Factor (EGF) on the Corneal Epithelium in Humans", *Albrecht v. Graefer Arch. Klin. exp. Ophthalmoloqie*, 210:159-165 (1979). In addition, ophthalmic preparations can be used in combination with corticosteroids to accelerate epithelial regeneration or healing of stromal wounds. Further, topical administration of biosynthetic human epidermal growth factor given in combination with an antibiotic (neomycin sulfate) and a synthetic steroid (dexamethasone phosphate) accelerate the rate of corneal epithelial regeneration and significantly increase the strength of full-thickness stromal incisions in primates. P. Woost et al., "Acceleration of Corneal Wound Healing", *Proc. Int. Soc. for Eve Research* III, 1984.

The amount of epidermal growth factor present in such ophthalmic preparations ranges from about 0.001% w/v to about 0.10% w/v of the composition. The epidermal growth factor employed can be naturally occurring, such as bovine, rat, porcine, mouse or human growth factor and the like, or it can be biosynthetic, such as recombinant human epidermal growth factor (rhEGF).

Other growth factors which can be employed in pharmaceutical and therapeutic compositions and stabilized by the method of this invention include methionine containing insulin-like growth factor I (IGF-I), transforming growth factor alpha precursor (TGF-αP), transforming growth factor beta (TGF-β), transforming growth factor beta precursor (TGF-βP), nerve growth factor (NGF), platelet-derived growth factor (PDGF), fibroblast growth factor (FGF), and vaccinia growth factor (VGF) as well as any methionine-containing fragments, precursors and analogs thereof. The quantities employed vary and are known by those skilled in the art.

The methionine is added to these compositions in amounts sufficient to significantly inhibit oxidation of the methionine residue(s) such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 10:1 to about 100:1. Accordingly, methionine is added to the composition in amounts such that its concentration ranges from about 0.01% w/v to about 1.0% w/v. Preferably, the final concentration of the added methionine ranges from about 0.01% w/v to about 0.3% w/v.

Adjuvants or pharmaceutically inactive ingredients can be added to the ophthalmic composition to further stabilize, preserve and maintain the composition. The adjuvants added to the composition are those which are typically added to aqueous ophthalmic preparations as practiced according to the art. For example, sodium chloride can be added at a concentration of about 0.9% w/v or less to assist in making the ophthalmic composition physiologically isotonic. Other components that optionally can be included in the composition include a buffer system composed of phosphates, citrates, acetates, lactates and the like as practiced in the art to maintain a pH of optimum stability. Sodium hydroxide, hydrochloric acid or acetic acid and the like can be added to adjust the composition to the desired pH and viscosity agents, such as sodium carboxymethyl cellulose, hydroxypropylmethyl cellulose or polyvinyl alcohol, at a concentration of about 2.0% w/v or less, and the like also can be added. Emulsifying agents such as povidone, at a concentration of about 5.0% w/v or less, and the like optionally can be added. Glycerin at a concentration of about 2.0% w/v to about 4% w/v can be added as a tonicity agent in situations where sodium chloride can not be used. Polymeric quaternary ammonium salts at a concentration of about 0.005% w/v to about 0.001% w/v can be added as preservatives. Other preservatives that are characteristically employed as such for ophthalmic preparations also can be included in compositions of this invention.

In addition to methionine, other stabilizing agents, such as albumin and edetate disodium (EDTA), can be added to further enhance the stability of the ophthalmic composition in addition to the beneficial effect of methionine. The amount of albumin can be added at concentrations of about 1.0% w/v or less. The edetate disodium can be added at a concentration of about 0.1% w/v or less. The edetate disodium acts as a scavenger of metal ions known to catalyze many oxidation reactions, thus providing an additional stabilizing agent.

Purified water USP is added to the ophthalmic preparation to bring the composition to its final volume. Purified or sterile water can be employed. The ophthalmic preparation then can be packaged in squeezable plastic containers made of low density polyethylene which is very permeable to oxygen. The added methionine inhibits the rapid oxidation of the methionine residue of the polypeptide which otherwise would occur, thus providing a more stable ophthalmic preparation having a longer therapeutic life.

In another embodiment of the present invention, epidermal growth factor, methionine and any of the foregoing optional pharmaceutical adjuvants can be dissolved in a minimal amount of purified water U.S.P. or other sterile water and incorporated into a semisolid dosage form, such as an ointment, cream or lotion, useful for treating or preventing eye conditions according to the methods as practiced in the art. As before, sufficient methionine (L, D or DL isomer) is added to the preparation to inhibit the methionine residue(s) from being oxidized to methionine sulfoxide. Typically, epidermal growth factor is present in such compositions in amounts of from about 0.001% w/w to about 0.01% w/w of the semisolid preparation and the methionine is added in amounts of from about 0.01% w/w to about 1.0% w/w. Preferably, the final concentration ranges from about 0.01% w/w to about 0.3% w/w.

Typical emollients in which the foregoing aqueous composition of methionine and polypeptide can be incorporated include white petrolatum U.S.P., mineral oil, and vegetable oils, such as olive oil, cottonseed oil and almond oil, and the like. Optional pharmaceutical adjuvants also can be added. The optional adjuvants can include surface active agents, such as sorbitans, polysorbates and the like; an antioxidant, such as butylated hydroxytoluene (BHT) and the like; solvents, such as a propylene glycol, glycerin and the like and suspending agents, such as magma of bentonite and the like. Emulsifying agents, such as isopropyl myristate, lanolin alcohol and the like also can be added to further stabilize the semisolid composition.

In still another embodiment of the present invention, methionine can be added to tissue storage media, such as cornea storage medium, comprising growth factors having an amino acid sequence which comprises at least one methionine residue. Sufficient methionine is added to the tissue storage media to inhibit the oxidation of the methionine residue in the growth factors to methionine sulfoxide.

Typically, the growth factors are added to a cornea storage medium in amounts generally ranging from about 1 picomolar to about 10 micromolar. Methionine (L, D or DL isomer) is characteristically added in amounts which range from about 0.001% w/v to about 0.005% w/v. Preferably, the concentration of methionine ranges from about 0.001% w/v to about 0.003% w/v.

Characteristically, the components comprising cornea storage media include an aqueous electrolyte solution (e.g. Gibco MEM or TC 199), a buffer system (e.g., bicarbonate plus hydroxyethyl piperidine ethanesulfonic acid, "HEPES") to maintain an essentially neutral pH of about 7.0 to about 7.4, an energy and carbon source (glucose and/or pyruvate), an antioxidant (glutathione or ascorbate), deturgescent (e.g., a polysaccharide such as carboxyalkyl cellulose, polyvinyl pyrrolidone, polyvinyl alcohol, hyaluronic acid and especially dextran sulfate), antibiotic (e.g., gentamicin, streptomycin and the like) and antimycotic (e.g., fungizone) agents, membrane stabilizing agents (e.g. vitamins A and B, retinoic acid and/or cofactors) and other optional components such as a glycosaminoglycan (Std. or purified, low molecular weight A, B or C heparin sulfate, keratan sulfate and/or dermatan sulfate; chondroitin sulfate (A, B or C isomer) or sodium hyaluronate), additional mitotic-enhancing agents, such as transferrin, selenous acid and linoleic acid, preservatives, such as the polymeric quaternary ammonium salts and the like.

The storage media also contain essential nutrients and minerals in at least the minimum concentration required for cell growth. In general, they contain inorganic salts, such as calcium, magnesium, iron, sodium and potassium salts of carbonates, nitrates, phosphates, chloride and the like, essential and nonessential amino acids, vitamins and other essential nutrients. Chemically defined basal nutrient media are commercially available, for example, from Gibco Laboratories (3175 Stanley Road, Grand Island, New York 14073) and Microbiological Associates (P.O. Box 127, Biggs Ford Road, Walkersville, Maryland 21793) under the names Eagle's minimal essential medium and TC 199, respectively. Eye tissue storage media have been adopted from these nutrient media. Commercially available cornea storage media useful in the present invention include MK, Dexsol TM, Optisol TM and Optisol Plus TM (obtainable from Chiron Ophthalmics, Irvine California).

The resulting cornea storage media are packaged in 20 ml glass containers. This makes for easy storage in tissue banks as well as convenient application of the media to ocular tissue. The added methionine stabilizes the polypeptides in the medium from rapid oxidation, thus prolonging the effective life of the preparation.

The invention is further illustrated by the following examples. Various modifications can be made without departure from the spirit and scope of the invention. Accordingly, it is not intended that the invention be limited except as by the intended claims.

Example I

Stability of Recombinant Human Epidermal Growth Factor (rhEGF) Acetate Solutions with Methionine at 4° C.

The following four formulations were prepared and filled in individual 6 ml clear low density polyethylene (LDPE) ophthalmic containers. Only 2 ml of each solution were placed in each container to allow for sufficient oxygen in the head space. A sufficient amount of 0.05M phosphate buffered saline was added to each formulation to maintain a pH of from about 7.0 to about 7.4. The recombinant human epidermal growth factor (rhEGF) acetate used was obtained from Chiron Corp., Emeryville, California.

| Formulation I: | 0.01% w/v rhEGF in 0.05M phosphate buffered saline with 0.1% w/v L-methionine USP, and 0.015% w/v EDTA USP, qs with a sufficient amount of purified water USP. |
|---|---|
| Formulation II: | 0.01% w/v rhEGF in 0.05M phosphate buffered saline with 0.1% w/v L-methionine USP, and 0.1% w/v EDTA USP, qs with a sufficient amount of purified water USP. |
| Formulation III: | 0.01% w/v rhEGF in 0.05M phosphate buffered saline with 0.015% w/v EDTA USP. |
| Formulation IV: | 0.01% w/v rhEGF in 0.05M phosphate buffered saline with 0.1% w/v EDTA USP. |

Each container was stored at 4° C. for a period of 105 days. Samples were withdrawn from each formulation on day 0, 14, 24, 30, 60 and 105 and assayed in a high performance liquid chromatograph (HPLC) to determine the percent oxidation of rhEGF to rhEGF methionine sulfoxide. Table I shows the percent oxidation rates of rhEGF. FIG. 1 presents the data from Table I graphically. It is clear that the addition of L-methionine reduced the rate of oxidation of rhEGF drastically. Formulation I showed a 1.4% increase in oxidized rhEGF in 105 days while Formulation III (without L-methionine) showed 17.7% oxidation in 105 days. Increasing the level of EDTA from 0.01% w/v to 0.1% w/v did not appear to further enhance the stability of rhEGF in the presence of L-methionine, while it appeared to enhance the stability of rhEGF in the absence of L-methionine.

Figure 3A:
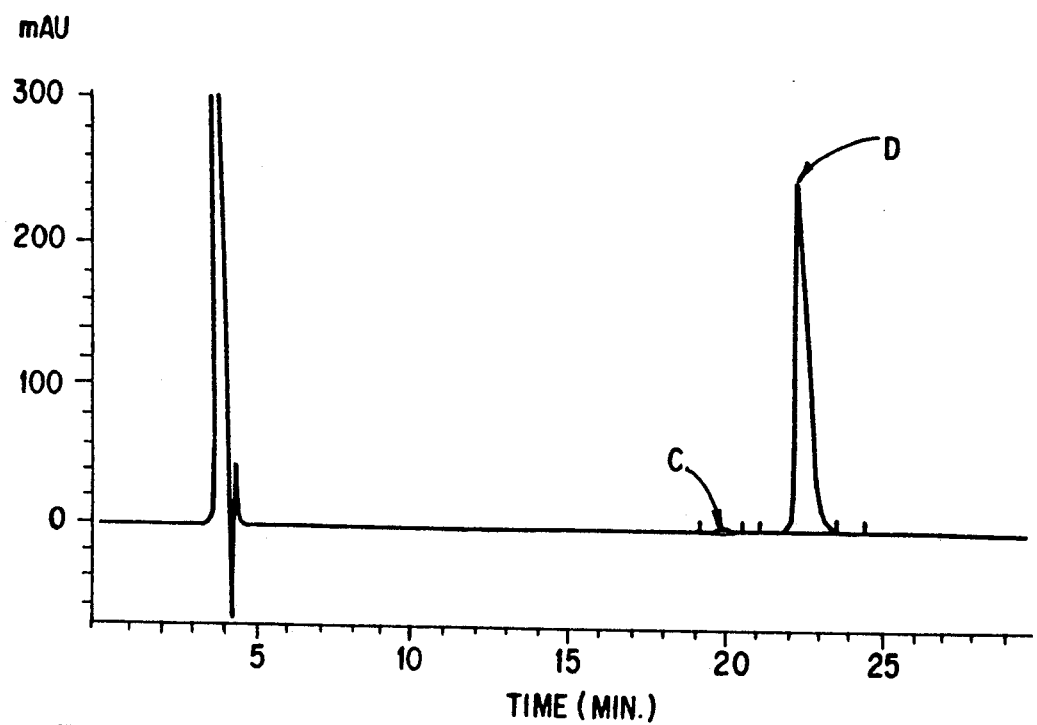
FIGS. 3A and 3B illustrate the high performance liquid chromatogram (HPLC) for a formulation of rhEGF and methionine at 4° C. on day 0 and on day 105, respectively.
Figure 3B:
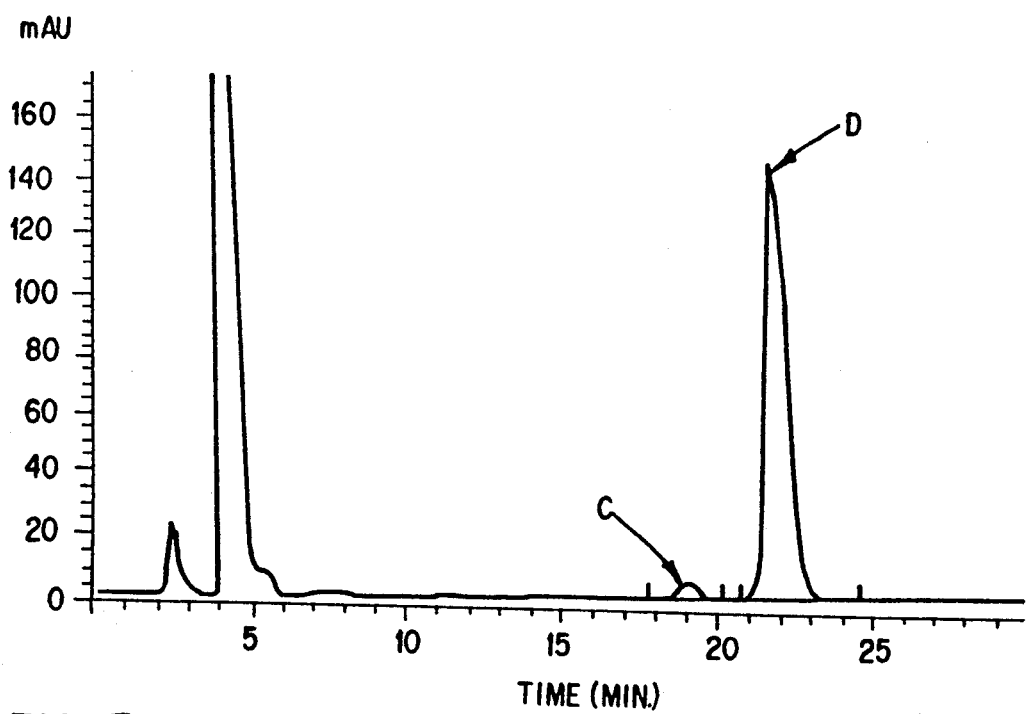
Figure 4A:
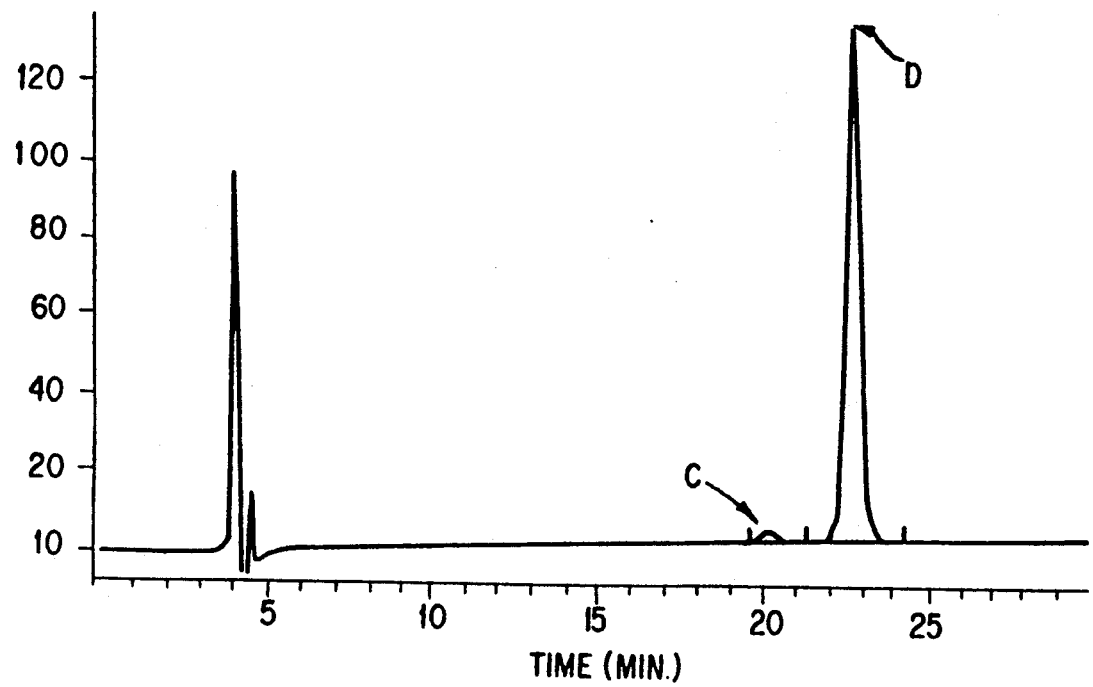
FIGS. 4A and 4B illustrate the high performance liquid chromatogram (HPLC) for a formulation of rhEGF without methionine at 4° C. on day 0 and on day 105.
Figure 4B:
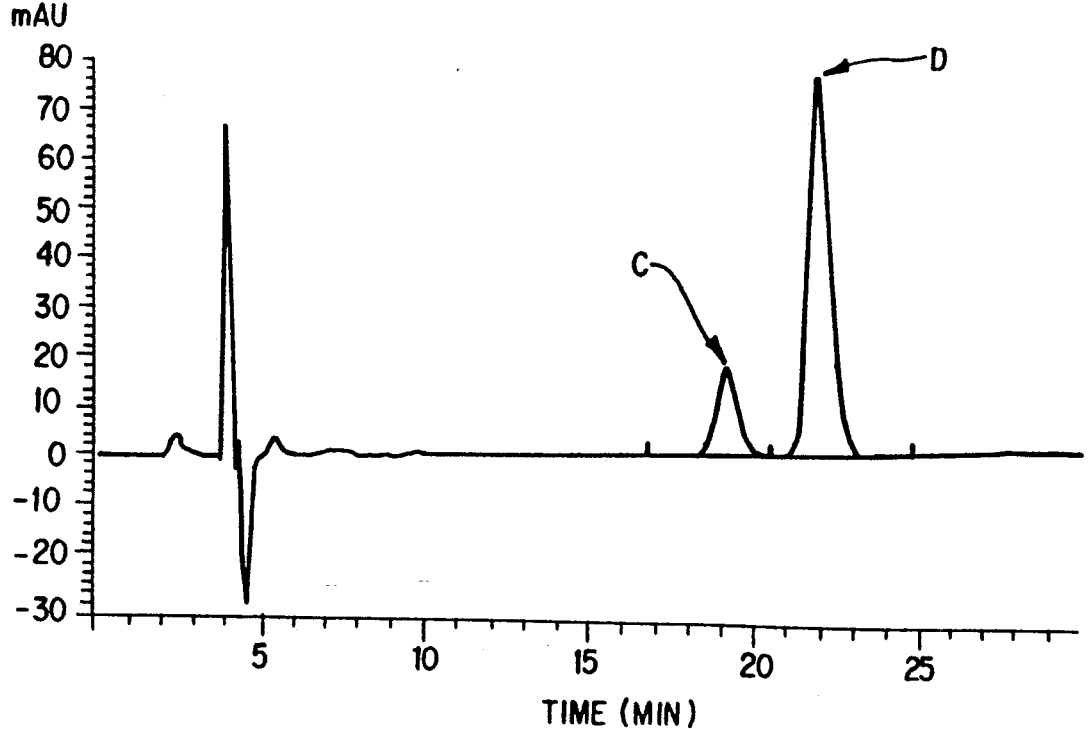

FIG. 3 and 4 show the HPLC chromatograms, milliabsorbance units (mAU) versus time, of the initial and aged (105 days) samples of Formulations I and III, respectively. The rhEGF is labeled peak D and the rhEGF methionine sulfoxide is labeled peak C. Comparison of the chromatograms in FIGS. 3A, 3B and 4A, 4B clearly shows that the addition of L-methionine reduced the amount of rhEGF oxidized to rhEGF methionine sulfoxide. The amount of rhEGF that oxidized to rhEGF methionine sulfoxide as seen in FIG. 4B was considerably more than the amount of rhEGF that oxidized to rhEGF methionine sulfoxide in FIG. 3B.

TABLE I

Percent Oxidation of rhEGF Acetate Formulations I-IV at 4° C.

| TIME (DAYS) | FORM. I | FORM. II | FORM. III | FORM. IV |
|---|---|---|---|---|
| 0 | 1.8% | 1.6% | 1.8% | 1.6% |
| 14 | 2.5 | 2.4 | | |
| 24 | | | 15 | 8.7 |
| 30 | 2.7 | 4.1 | | |
| 60 | 2.7 | 3.2 | 17.4 | 12.5 |
| 105 | 3.2 | 3.6 | 19.5 | 13.1 |

Formulation I: with 0.1% L-methionine, with 0.015% EDTA
Formulation II: with 0.1% L-methionine, with 0.1% EDTA
Formulation III: without L-methionine, with 0.015% EDTA
Formulation IV: without L-methionine, with 0.1% EDTA

Example II

Stability of Recombinant Human Epidermal Growth Factor (rhEGF) Acetate Solutions with Methionine at Room Temperature.

Figure 2:
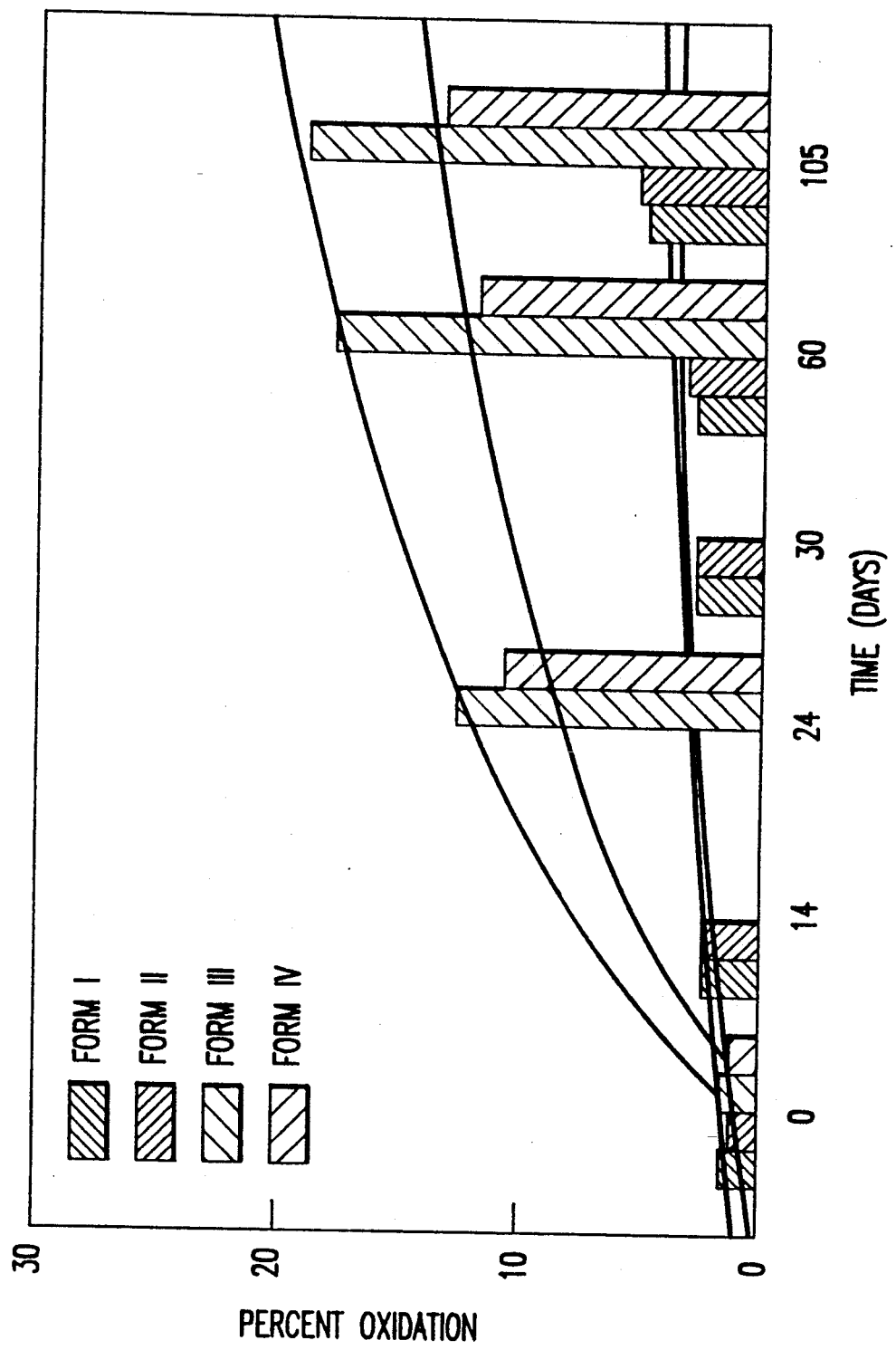
FIG. 2 illustrates the oxidation rates of four different formulations of recombinant human epidermal growth factor (rhEGF) acetate at room temperature (20° C.) over a 105 day time period.

Four formulations were prepared and tested as in Example I except that the formulations were stored at room temperature (23°+2° C.). Table II shows the percent oxidation rates at room temperature. It is clear that the addition of L-methionine reduced the rate of oxidation of rhEGF drastically even at room temperature. Formulation I showed a 2.8% increase in oxidized rhEGF in 105 days while Formulation III (without L-methionine) showed a 16.5% increase in oxidized rhEGF over the same time period. FIG. 2 graphically presents the data in Table II. The addition of methionine to a formulation containing rhEGF clearly stabilized the rhEGF against oxidation.

TABLE II

Percent Oxidation of rhEGF Acetate Formulations I-IV at Room Temperature

| TIME (DAYS) | FORM. I | FORM. II | FORM. III | FORM. IV |
|---|---|---|---|---|
| 0 | 1.8% | 1.6% | 1.8% | 1.6% |
| 14 | 2.5 | 2.4 | | |
| 24 | | | 12.5 | 10.5 |
| 30 | 2.9 | 2.9 | | |
| 60 | 2.6 | 3.1 | 17.3 | 11.3 |
| 105 | 4.6 | 5.1 | 18.3 | 12.5 |

Formulation I: with 0.1% L-methionine, with 0.015% EDTA
Formulation II: with 0.1% L-methionine, with 0.1% EDTA
Formulation III: without L-methionine, with 0.015% EDTA
Formulation IV: without L-methionine, with 0.1% EDTA

Example III

Recombinant Human Epidermal Growth Factor (rhEGF) Ophthalmic Solution, 0.01% w/v.

The following ingredients were sterile filtered into sterile low density polyethylene (LDPE) ophthalmic containers to form a pharmaceutically stable and effective ophthalmic solution. The resulting ophthalmic solutions were considerably more stable and had a longer therapeutic life than if the methionine had not been added. Table III discloses the results of the oxidation rates in two batches of a 0.01% EGF solution with methionine. Clearly, methionine reduced the rate of methionine oxidation of the EGF in both batches to an insignificant level.

| Ingredient | Concentration, percent w/v | |
|---|---|---|
| rhEGF* | | 0.01 |
| Sodium Chloride | USP | 0.55 |
| Sodium Phosphate Monobasic Monohydrate | USP | 0.19 |
| Sodium Phosphate Dibasic Heptahydrate | USP | 0.96 |
| Edetate Disodium (EDTA) | USP | 0.015 |
| L-Methionine | USP | 0.10 |
| Purified Water | USP | qs 100 |

TABLE III 0.01% w/v EGF Ophthalmic Solution
Percent of EGF Oxidized at 4° C.

| Time (Days) | 0.01% w/v EGF Sol. with methionine Lot #IPL0001 | 0.01% w/v EGF Sol. with methionine Lot #39-60 |
|---|---|---|
| Initial | 1.02 | 0.151 |
| 30 | 1.10 | 0.966 |
| 60 | 2.28 | 1.172 |
| 200 | 2.19 | 1.645 |

*Obtained from Chiron Corp., Emeryville, California.

Example IV

Recombinant Human Epidermal Growth Factor (rhEGF) Ophthalmic Solution, 0.003% w/v.

The following ingredients were sterile filtered into a low density polyethylene (LDPE) ophthalmic bottle to form a pharmaceutically stable and effective ophthalmic solution. The resulting ophthalmic solution was considerably more stable and had a longer therapeutic life than if the methionine had not been added. After 95 days storage at 4° C. the percent of EGF oxidized increased from 2.55 to 3.88, an increase of only 1.33 percent.

| Ingredient | Concentration, percent w/v | |
| --- | --- | --- |
| rhEGF* | | 0.003 |
| Sodium Chloride | USP | 0.55 |
| Sodium Phosphate Monobasic Monohydrate | USP | 0.19 |
| Sodium Phosphate Dibasic Heptahydrate | USP | 0.96 |
| L-Methionine | USP | 0.10 |
| Purified Water | USP | qs 100 |

*Obtained from Chiron Corp., Emeryville, California.

Example V

Recombinant Human Epidermal Growth Factor (rhEGF) Ophthalmic Ointment, 0.01% w/w.

The following ingredients are combined to form a pharmaceutically stable and effective ophthalmic ointment that can be applied to the eyes to treat herpetic lesions or other epithelial defects. The components are dissolved in a minimal amount of purified water U.S.P. The resulting solution is then slowly added to white petrolatum according to the methods practiced in the art to form a stable water in oil emulsion. The resulting ophthalmic ointment is considerably more stable than if the methionine is not added.

| Ingredient | Concentration, percent w/w | |
| --- | --- | --- |
| rhEGF | | 0.01 |
| Lanolin Alcohol | | 5.00 |
| L-Methionine | USP | 0.01 |
| Purified Water | USP | a sufficient amount to dissolve the foregoing ingredients |
| White Petrolatum | USP | qs 100 |

We claim:

1. A method of inhibiting oxidation of a liquid or semi-liquid composition of a polypeptide having an amino acid sequence comprising at least one methionine residue which comprises adding methionine to the composition in an amount sufficient to inhibit oxidation of the at least one methionine residue, said amount being between about 0.01% w/v and 0.3% w/v.

2. The method according to claim 1, wherein the amount of methionine added to the composition is such that the ratio of added methionine to the at least one methionine residue is from about 10:1 to about 100:1.

3. The method according to claim 1, wherein the composition comprises a plurality of methionine residues and methionine is added to the composition in an amount sufficient to inhibit oxidation of at least about 70% of the methionine residues present in the composition during the period in which the composition will be stored and used.

4. The method according to claim 1, wherein the polypeptide is a growth factor.

5. The method according to claim 4, wherein the growth factor comprises one of epidermal growth factor, insulin-like growth factor I, nerve growth factor, transforming growth factor alpha precursor, transforming growth factor beta, transforming growth factor beta precursor, fibroblast growth factor, vaccinia growth factor, platelet derived growth factor, or a methionine containing biologically active fragment, precursor or analog of one of these growth factors.

6. The method according to claim 5, wherein the growth factor comprises bovine, porcine, rat, mouse or human growth factor.

7. The method according to claim 5, wherein the growth factor comprises natural or recombinant growth factor.

8. The method according to claim 5, wherein the composition is a liquid, the growth factor comprises epidermal growth factor in a sufficient amount such that its concentration ranges from about 0.001% w/v to about 0.1% w/v and the methionine is added such that its concentration ranges from about 0.01% w/v to about 0.3% w/v.

9. The method according to claim 5, wherein the composition is in the form of a semi-solid, the growth factor comprises epidermal growth factor in a sufficient amount such that its concentration ranges from about 0.001% w/w to about 0.1% w/w and the methionine is added such that its concentration ranges from about 0.01% w/w to about 0.3% w/w.

10. The method according to claim 1, wherein the liquid or semi-solid composition further comprises one or more pharmaceutically acceptable adjuvants.

11. The method according to claim 10, wherein the composition is a liquid and the pharmaceutically acceptable adjuvants comprise one or more of sodium chloride, phosphates, citrates, acetates, lactates, edetate disodium, povidone, polyvinyl alcohol, glycerin, sodium carboxymethyl cellulose, hydroxypropylmethyl cellulose, sodium hydroxide, hydrochloric acid, acetic acid, albumin, or quaternary ammonium salts.

12. The method according of claim 10, wherein the composition is a semi-solid and the pharmaceutically acceptable adjuvants comprise one or more of white petrolatum, mineral oil, vegetable oils, sorbitans, polysorbates, butylated hydroxytoluene, propylene glycol, glycerin, magma of bentonite, isopropyl myristate, lanolin alcohol or edetate disodium.

13. A stable liquid or semi-solid pharmaceutical or therapeutic preparation which comprises a polypeptide having an amino acid sequence which compiles at least one methionine residue and methionine, wherein the methionine is present at a concentration sufficient to inhibit oxidation of the at least one methionine residue of the polypeptide, said concentration being between about 0.01% w/v and 0.3% w/v.

14. A stable liquid pharmaceutical preparation in accordance with claim 13, wherein the liquid preparation is an aqueous ophthalmic solution comprising an epidermal growth factor at a concentration range of from about 0.001% w/v to about 0.10% w/v and further comprising methionine at a concentration range of from about 0.01% w/v to about 0.3% w/v.

15. A stable semi-solid pharmaceutical preparation in accordance with claim 13, wherein the semi-solid preparation is a cream, ointment or lotion comprising an epidermal growth factor at a concentration range of from about 0.001% w/w to about 0.01% w/w and further comprising methionine at a concentration range of about 0.01% w/w to about 0.3% w/w.

16. A stable liquid or semi-solid preparation of claim 13, further comprising one or more pharmaceutically acceptable adjuvants.

17. A stable liquid pharmaceutical preparation in accordance with claim 16, wherein the pharmaceutically acceptable adjuvants comprise one or more of sodium chloride, phosphates, citrates, acetates, lactates, edetate disodium, povidone, polyvinyl alcohol, glycerin, sodium carboxymethyl cellulose, hydroxypropylmethyl cellulose, dosium hydroxide, hydrochloride acid, acetic acid, albumin, or quaternary ammonium salts.

18. A stable semi-solid pharmaceutical preparation in accordance with claim 16, wherein the pharmaceutically acceptable adjuvants comprise one or more of white petrolatum, mineral oil, vegetable oils, sorbitans, polusorbates, butylated hudroxytoluene, propylene glycol, glycerin, magma of bentionite, isopropyl myristate, lanolin alcohol or edetate disodium.

19. A stable liquid or semi-solid pharmaceutical preparation in accordance with claim 13, wherein the methionine containing peptides comprise one of epidermal growth factor, insulin-like growth factor I, nerve growth factor, transforming growth factor alpha precursor, transforming growth factor beta, transforming growth factor beta precursor, fibroblast growth factor, vaccinia growth factor, platelet derived growth factor or a methionine containing biologically active fragment, analog or precursor of one of these growth factors.

20. A stable liquid or semi-solid pharmaceutical preparation in accordance with claim 19, wherein the growth factors are bovine, porcine, rat, mouse or human.

21. A stable liquid or semi-solid pharmaceutical preparation in accordance with claim 19, wherein the growth factors are natural, synthetic or recombinant.

22. A method of stabilizing an aqueous-based tissue storage medium which comprises a tissue growth factor having an amino acid sequence comprising at least one methionine residue which comprises adding methionine to the medium in an amount sufficient to inhibit oxidation of the at least one methionine residue, said amount being between about 0.01% w/v and 0.3% w/v.

23. The method according to claim 22, wherein the growth factor comprises one or more of epidermal growth factor, insulin-like growth factor I, nerve growth factor, transforming growth factor beta, fibroblast growth factor, vaccinia growth factor, or a methionine containing biologically active fragment, analog or precursor of one of the growth factors.

24. The method according to claim 23, wherein the composition further comprises at least one component selected from the group consisting of electrolytes, antioxidants, buffers, energy source, deturgescents, antibiotics and antimycotics.

25. The method according to claim 22, wherein the storage medium is eye tissue storage medium.

* * * * *

UNITED STATES PATENT AND TRADEMARK OFFICE
CERTIFICATE OF CORRECTION

PATENT NO. : 5,272,135
DATED : December 21, 1993
INVENTOR(S) : Harun Takruri

It is certified that error appears in the above-indentified patent and that said Letters Patent is hereby corrected as shown below:

Col. 1, line 51, "Chao" should be --Chah--.

Col. 3, line 21, after "105" insert --, respectively--.

Col. 4, line 6, "Eve" should be --Eye--.

Col. 10, line 42, "hydroxyproprylmethyl" should be --hydroxypropylmethyl--.

Col. 11, line 15, "dosium" should be --sodium--, and "hydrochloride" should be --hydrochloric--.

Col. 11, line 22, "polusorbates" should be --polysorbates--, and "hudroxytoluene" should be --hydroxytoluene--.

Col. 11, line 23, "bentionite" should be --bentonite--.

Signed and Sealed this

Second Day of August, 1994

Attest:

BRUCE LEHMAN

Attesting Officer    Commissioner of Patents and Trademarks